United States Patent
Shraibom (10) Patent No.: US 8,541,382 B2
(45) Date of Patent: Sep. 24, 2013

(54) CARDIAC GLYCOSIDE ANALOGS IN COMBINATION WITH EMODIN FOR CANCER THERAPY

(75) Inventor: Nadav Shraibom, Herzelia (IL)

(73) Assignee: Sirbal Ltd., Limassol (CY)

( * ) Notice: Subject to any disclaimer, the term of this patent is extended or adjusted under 35 U.S.C. 154(b) by 0 days.

(21) Appl. No.: 13/018,435

(22) Filed: Feb. 1, 2011

(65) Prior Publication Data

US 2012/0122807 A1 May 17, 2012

Related U.S. Application Data

(60) Provisional application No. 61/413,430, filed on Nov. 13, 2010.

(51) Int. Cl.
*A01N 45/00* (2006.01)

(52) U.S. Cl.
USPC .......................................................... 514/26

(58) Field of Classification Search
None
See application file for complete search history.

(56) References Cited

U.S. PATENT DOCUMENTS

| | | |
|---|---|---|
| 5,872,103 A | 2/1999 | Belletti |
| 6,197,754 B1 | 3/2001 | Hung et al. |
| 6,740,665 B1 | 5/2004 | Murali et al. |
| 6,812,255 B2 | 11/2004 | Palu' et al. |
| 7,268,162 B2 | 9/2007 | Palu et al. |
| 7,358,222 B2 | 4/2008 | Nadel et al. |
| 7,381,535 B2 | 6/2008 | Perez et al. |
| 7,393,656 B2 | 7/2008 | Perez et al. |
| 7,563,584 B2 | 7/2009 | Perez et al. |
| 7,695,926 B2 | 4/2010 | Perez et al. |
| 7,790,905 B2 | 9/2010 | Tawa et al. |
| 2003/0211180 A1 | 11/2003 | Cheng et al. |
| 2005/0008664 A1 | 1/2005 | Claxton et al. |
| 2005/0026849 A1 | 2/2005 | Singh et al. |
| 2005/0196473 A1 | 9/2005 | Cheng et al. |
| 2006/0205679 A1 | 9/2006 | Streeper et al. |
| 2007/0191262 A1 | 8/2007 | Racila et al. |
| 2008/0152700 A1 | 6/2008 | Sheikhnejad et al. |
| 2008/0220441 A1 | 9/2008 | Birnbaum et al. |
| 2009/0018088 A1 | 1/2009 | Valdes, Jr. et al. |
| 2009/0143279 A1 | 6/2009 | Mootha et al. |
| 2009/0215042 A1 | 8/2009 | Sella-Tavor et al. |
| 2009/0269772 A1 | 10/2009 | Califano et al. |
| 2010/0068198 A1 | 3/2010 | Mijatovic et al. |
| 2010/0092585 A1 | 4/2010 | Smothers |
| 2010/0144647 A1 | 6/2010 | Kratz et al. |
| 2010/0167286 A1 | 7/2010 | Reijo Pera et al. |

FOREIGN PATENT DOCUMENTS

| | | |
|---|---|---|
| CN | 1370587 A | 3/2002 |
| CN | 1370587 A | 9/2002 |
| CN | 1796400 A | 7/2006 |
| CN | 101362702 A | 9/2008 |
| CN | 101362702 A1 | 2/2009 |
| JP | 6-321795 A | 11/1994 |
| KR | 100221762 B1 | 9/1999 |
| MX | 2010005081 A | 6/2010 |
| RU | 2008107585 A | 9/2009 |
| SG | 60053 A1 | 2/1999 |
| WO | 0166123 A2 | 9/2001 |
| WO | 2004/052294 A2 | 6/2004 |
| WO | 2006053049 A | 5/2006 |
| WO | 2007130124 A | 11/2007 |
| WO | 2012/063134 A2 | 5/2012 |

OTHER PUBLICATIONS

Khan et al. From: ASCO "Journal of Clinical Oncology, 2007 ASCO Annual Meeting Proceedings Part I. vol. 25, No. 18S (Jun. 20 Supplement), 2007: 8573" (abstract). Retrieved from the Internet on: Jan. 12, 2013. <http://www.asco.org/ASCOv2/Meetings/Abstracts?&vmview=abst_detail_view&confID=47&abstractID=35416>.*
Miller, L. "Rhubarb Root and Rhizome" from Acupuncture.com. Internet Archive Date: Feb. 10, 2006 [Retrieved from the Internet on: Jan. 12, 2013]. Retrieved from: <URL: http://web.archive.org/web/20060210091558/http://www.acupuncture.com/herbs/cancerherb.htm>.*
Luis Fayad, M.D. and Susan O'Brien, M.D., Chronic Lymphocytic Leukemia and Associated Disorders, Medical Oncology: A Comprehensive Review, 1995.
Michael J. Keating, et al., Biology and Treatment of Chronic Lymphocytic Leukemia, American Society of Hematology, Hematology 2003, 153-175.
Ranjit Thomas, et al., Spontaneous Clinical Regression in Chronic Lymphocytic Leukemia, British Journal of Haematology, 2002, 116, 341-345.
Dragomir Marisavljevic, et al., Spontaneous Clinical Remission of Chronic Lymphocytic Leukemia, Haema 2003; 6(3): 394-397.
Upshaw JD, Jr., et al., Spontaneous Remission of B cell Chronic Lymphocytic Leukemia associated with T Lymphocytic Hyperplasia in bone marrow, South Med J. 2002 Jun. 1995(6): 647-9.
Wiernik PH, Second neoplasms in patients with chronic lymphocytic leukemia, Current Treat Options Oncol. Jun. 2004; 5(3):215-23.
W. L. Wendy Hsiao, Liang Liu, The Role of Traditional Chinese Herbal Medicines in Cancer Therapy—from TCM Theory to Mechanistic Insights, Planta Med 2010; 76: 1118-1131.

(Continued)

*Primary Examiner* — Amy L Clark
(74) *Attorney, Agent, or Firm* — SF Bay Area Patents, LLC; Andrew V. Smith (57) ABSTRACT

A method and medicine for treating leukemia or other cancer includes administering to a patient diagnosed with leukemia or other cancer a treatment regimen that includes periodic doses of a combination of emodin and digoxin.

40 Claims, 7 Drawing Sheets

(56) References Cited

OTHER PUBLICATIONS

PCT Notification of Transmittal of the International Search Report and the Written Opinion of the International Searching Authority, or the Declaration, for PCT Application No. PCT/IB2011/003078, report dated Jun. 8, 2012, 20 Pages.

Non-Final Rejection, dated May 30, 2012, for U.S. Appl. No. 13/218,432, filed Aug. 25, 2011.

Translation of Japanese published patent application No. JP 06-321795 A, Derwent Information Ltd., 2 pages, Nov. 22, 1994 (publication date).

Translation of Japanese published patent application No. JP 06-321795 A, machine translation, 6 pages, Nov. 22, 1994, (publication date).

Translation of Singapore published patent application No. SG 60053 A1, Derwent Information Ltd., 2 pages.

Non-Final Rejection, dated Jul. 31, 2012, for U.S. Appl. No. 13/218,437, filed Aug. 25, 2011, Publication Date: Feb. 22, 1999.

Translation of Chinese published patent application No. CN 1796400 A, Derwent Information Ltd., 2 pages, Publication date: Jul. 5, 2006.

* cited by examiner

CARDIAC GLYCOSIDE ANALOGS IN COMBINATION WITH EMODIN FOR CANCER THERAPY

PRIORITY

This application claims the benefit of priority to U.S. provisional patent application No. 61/413,430, filed Nov. 13, 2010, which is hereby incorporated by reference.

BACKGROUND OF THE INVENTION

1. Field of the Invention

The present invention relates generally to cancer therapeutics. More specifically it concerns the use of cardiac glycosides such as Digoxin and Quabain in combination with Emodin and its analogs for the treatment of cancer.

2. Description of the Related Art

Herbal medicines are still prevalent, and serve the medicinal needs of a large population around the world. The global herbal medicine market is currently worth around $30 billion. 1 There is an increased effort for the isolation of bioactive phytochemicals from herbs for their possible usefulness in the control of various ailments. Determining molecular structure and mechanisms of action of bioactive phytochemicals are equally important for providing the evidence for their efficacy as well as herbal preparations, which could also potentially lead to the pharmaceutical development of synthetic or semi-synthetic drugs.2View Record in ScopusCited By in Scopus (28)2 About herbal medicines in cancer studies, several previous studies demonstrate that certain phytochemicals present in medicinal herbs exert anti-cancer activities. Among three structurally related anthraquinones, including emodin, physcion, and chrysophanol, emodin showed the most potent cytotoxic effects on tumor cells. Emodin (1,3,8-trihydroxy-6-methylanthraquinone) and aloe-emodin, 1,8-dihydroxy-3-hydroxymethyl-9,10-anthracene-dione as shown a chemotherapeutic activity in vitro and in animal models for the treatment of various types of cancers, including bladder cancer,3 lung cancer,4 and hepatoma.5, and leukemia. Aloe-emodin is a natural anthraquinone compound that is present in some traditional medicinal plants such as Rhei Rhizoma and Rheum palmatum, Interestingly, aloe-emodin has been found to have lesser cytotoxicity towards the normal human cells.6

Plant-derived cardiac glycosides such as digoxin are used for the treatment of congestive heart failure and other cardiac disorders (1). Their main pharmacologic actions are mediated through inhibition of the sodium pump, Na+- and K+-dependent ATPase (NKA) 1 (EC 3.6.3.9) (2). NKA, a ubiquitous membrane cationic transporter protein, controls normal membrane potential in all eukaryotic cells by maintaining high K+ and low Na+ concentrations. It consists of a catalytic subunit and a β glycoprotein subunit (3). Studies have suggested that plant-derived cardiac glycosides regulate some cellular processes, such as proliferation and apoptosis, in a variety of cancer cells (4)(5)(6)(7).

INCORPORATION BY REFERENCE

What follows is a cite list of references which are, in addition to those references cited above and below herein, and including that which is described as background, the invention summary, brief description of the drawings, the drawings and the abstract, hereby incorporated by reference into the detailed description of the preferred embodiments below, as disclosing alternative embodiments of elements or features of the preferred embodiments not otherwise set forth in detail below. A single one or a combination of two or more of these references may be consulted to obtain a variation of the preferred embodiments described in the detailed description below. Further patent, patent application and non-patent references are cited in the written description and are also incorporated by reference into the preferred embodiment with the same effect as just described with respect to the following references:

U.S. Pat. Nos. 5,872,103, 6,197,754, 6,740,665, 6,812,255, 7,268,162, 7,358,222, 7,381,535, 7,393,656, 7,563,584, 7,695,926, 7,790,905, and United States published applications no. 2003/0211180, 2005/0026849, 2005/0196473, 2006/0205679, 2007/0191262, 2008/0152700, 2008/0220441, 2009/0018088, 2009/0143279, 2009/0215042, 2009/0269772, 2010/0068198, 2010/0092585, 2010/0144647, 2010/0167286; and PCT and foreign published applications no. WO/0166123, WO2004/052294, WO2006/053049, WO2007/130124; RU2008107585; MX2010005081; KR100221762; CN01362702; CN1370587; and Citations: Chronic Lymphocytic Leukemia by the Leukemia & Lymphoma Society, Medifocus.com Medifocus Guide on Chronic Lymphocytic Leukemia;

RANJIT THOMAS, et al., Spontaneous Clinical Regression in Chronic Lymphocytic Leukemia, British Journal of Haematology, 2002, 116, 341-345;

DRAGOMIR MARISAVLJEVIC, et al., Spontaneous Clinical Remission of Chronic Lymphocytic Leukemia, Haema 2003; 6(3): 394-397;

UPSHAW J D, Jr., et al., Spontaneous Remission of B cell Chronic Lymphocytic Leukemia associated with T Lymphocytic Hyperplasia in bone marrow, South Med J. 2002 June 1995(6): 647-9;

WIERNIK P H, Second neoplasms in patients with chronic lymphocytic leukemia, Current Treat Options Oncol. 2004 June; 5(3):215-23;

LUIS FAYAD, M. D. and SUSAN O'BRIEN, M. D., Chronic Lymphocytic Leukemia and Associated Disorders, Medical Oncology: A Comprehensive Review, 1995;

MICHAEL J. KEATING, et al., Biology and Treatment of Chronic Lymphocytic Leukemia, American Society of Hematology, Hematology 2003, 153-175;

G E MARTI, et al., Descriptive Epidemiology of Chronic Lymphocytic Leukemia (CLL).

DETAILED DESCRIPTION OF THE PREFERRED EMBODIMENTS

A method of treating leukemia or other cancer is provided. The treatment includes administering to a patient diagnosed with the leukemia or other cancer a regimen that includes periodic doses of a combination of emodin and digoxin.

The treatment method may include periodic doses including approximately 5 ug/ml or 10 ug/ml or more of Emodin, along with respectively 0.05 ug/ml or 0.10 ug/ml or more of digoxin. Other combinations may be used in the treatment, including combining 5 ug/ml or more of emodin with at least approximately 0.10 ug/ml digoxin, or at least approximately 10 ug/ml emodin with at least approximately 0.10 ug/ml digoxin, or more than 5 ug/ml of emodin with at least approximately 0.05 ug/ml digoxin, or at least approximately 10 ug/ml emodin and at least approximately 0.05 ug/ml digoxin. Other combinations may be used and prescribed by physicians depending on factors such variances in weight, age, gender, family or patient history, or other characteristics specific to patients.

The treatment regimen may include once or twice daily doses, or two or more weekly doses weekly or otherwise. Doses may be taken more than once or twice a day, while the amounts of each dose would be determined according to the periodicity of the treatments.

Methods of preparing leukemia or other cancer treatment medicines are also provided, including preparing a cocktail including a combination of emodin and digoxin.

A leukemia or other cancer treatment medicine is also provided, including a cocktail including a combination of emodin and digoxin.

The present invention is directed to novel therapeutic applications of cardiac glycosides such as digoxin and quabain alone or in combination with Emodin and its analogs for the treatment of cancer. More specifically blood cancers. Unexpectedly, the present invention discloses, for the first time, that digoxin synergize with emodin to stimulate cancer cell death.

Figure 1:
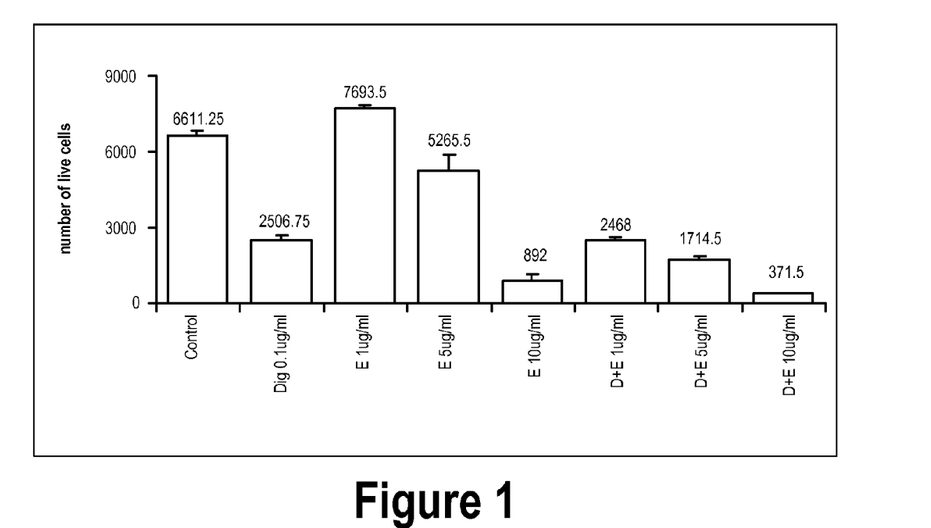
FIG. 1 illustrates the effect of on proliferation of digoxin, Emodin, and their combination on NB4 leukemic cells.

FIG. 1 illustrates the effect of on proliferation of digoxin, Emodin, and their combination on NB4 leukemic cells. The results represent average of triplicates±STDEV. The percentage of life and death cells was done using staining for PI for death cells and the number of lived cells was determined by FACS.

Figure 2:
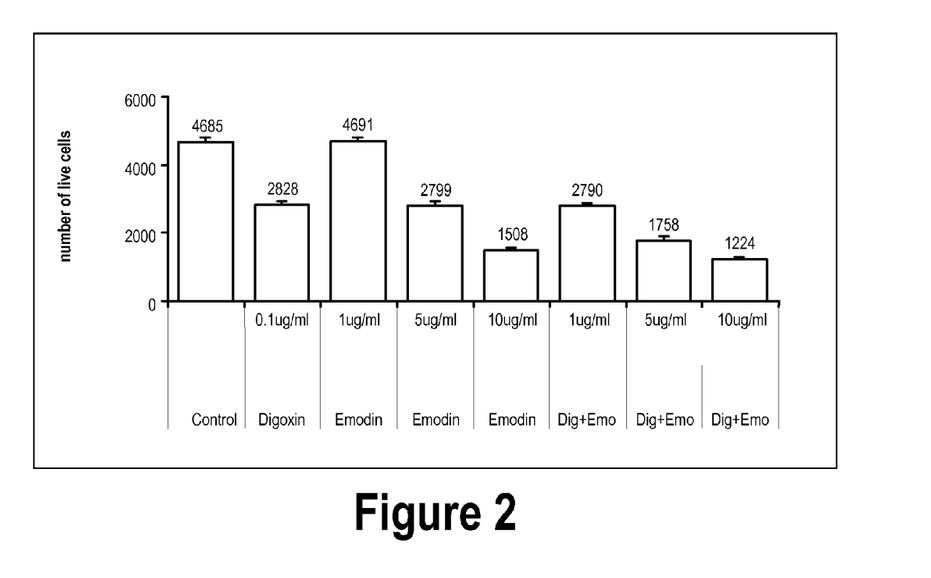
FIG. 2 illustrates the effect of on proliferation of digoxin, Emodin, and their combination on HL-60 leukemic cells.

FIG. 2 illustrates the effect of on proliferation of digoxin, Emodin, and their combination on HL-60 leukemic cells. The results represent average of triplicates±STDEV. The percentage of life and death cells was done using staining for PI for death cells and the number of lived cells was determined by FACS.

Figure 3:
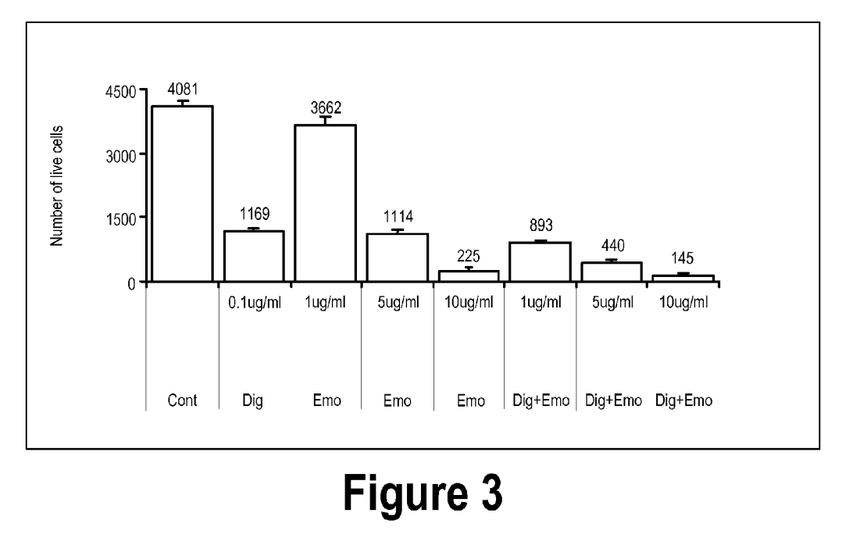
FIG. 3 illustrates the effect of on proliferation of digoxin, Emodin, and their combination on Jurkat T cell leukemic cells.

FIG. 3 illustrates the effect of on proliferation of digoxin, Emodin, and their combination on Jurkat T cell leukemic cells. The results represent average of triplicates±STDEV. The percentage of life and death cells was done using staining for PI for death cells and the number of lived cells was determined by FACS.

Figure 4:
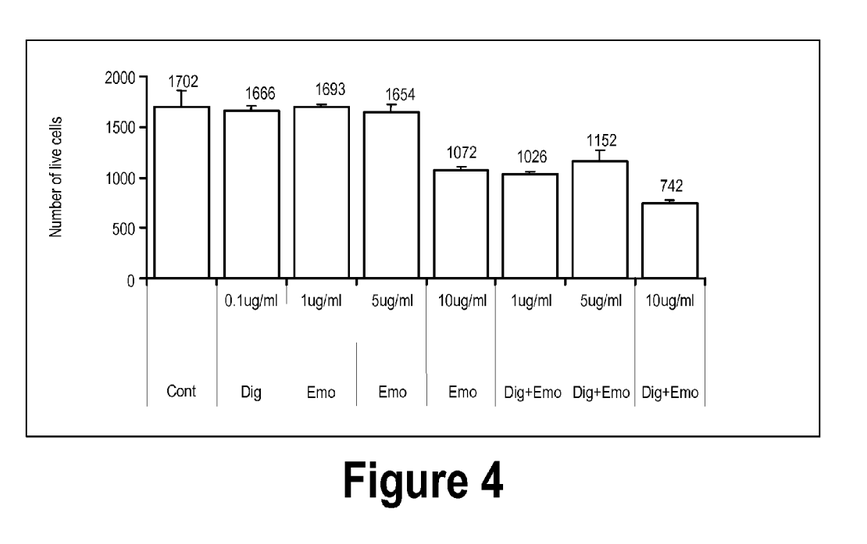
FIG. 4 illustrates the effect of on proliferation of digoxin, Emodin, and their combination on HT29 colon cancer cells.

FIG. 4 illustrates the effect of on proliferation of digoxin, Emodin, and their combination on HT29 colon cancer cells. The results represent average of triplicates±STDEV. The percentage of life and death cells was done using staining for PI for death cells and the number of lived cells was determined by FACS.

Figure 5:
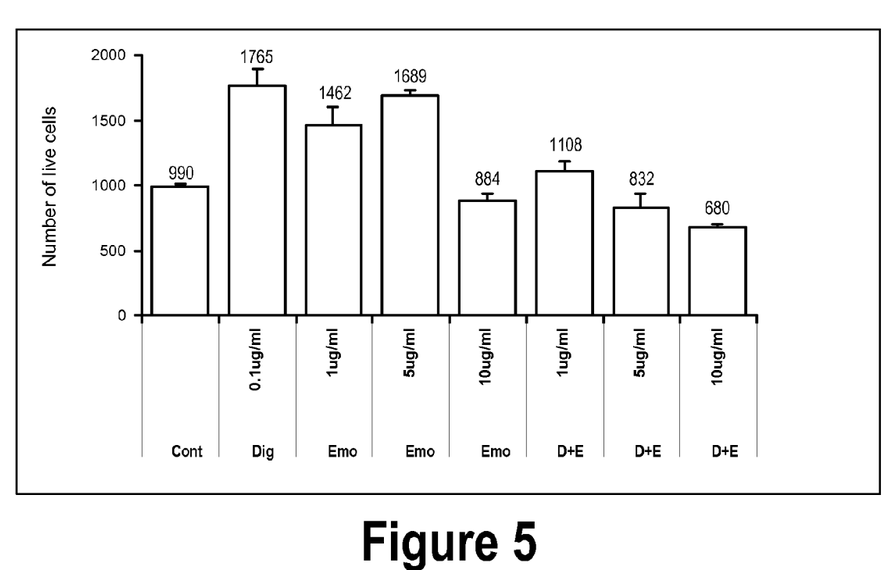
FIG. 5 illustrates the effect of proliferation of digoxin, Emodin, and their combination on PC3 prostate tumor cells.

FIG. 5 illustrates the effect of on proliferation of digoxin, Emodin, and their combination on PC3 prostate tumor cells. The results represent average of triplicates±STDEV. The percentage of life and death cells was done using staining for PI for death cells and the number of lived cells was determined by FACS.

Figure 6:
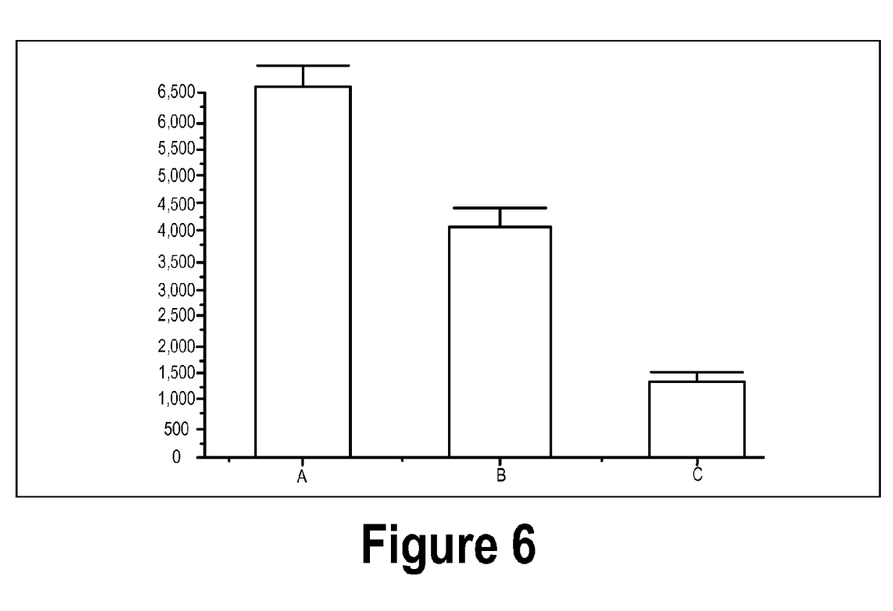
FIG. 6 illustrates the effect of proliferation of Digoxin, Emodin and their combination on MDA 435 Breast Cancer cells.

FIG. 6 illustrates the effect of proliferation of digoxin, Emodin and their combination on MDA 435 are cell line of Breast Cancer. In the in vitro experiments, there is a dependency on concentration.

Figure 7:
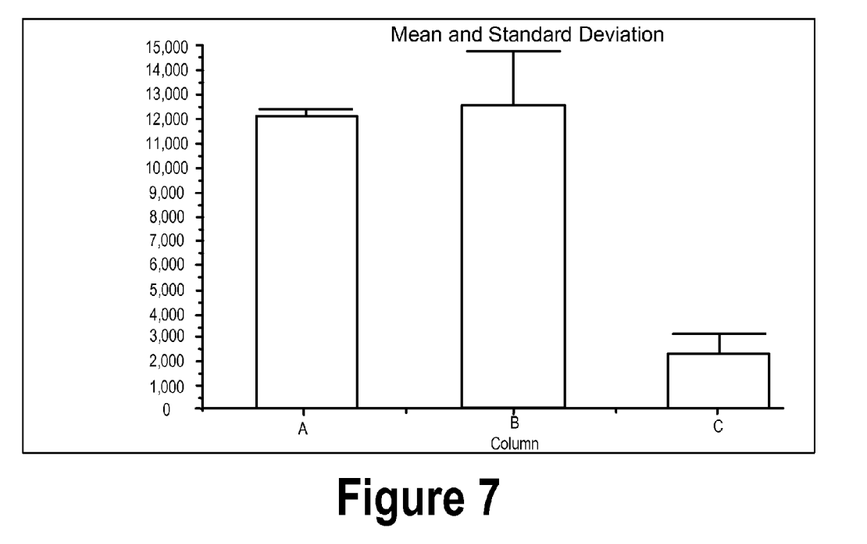
FIG. 7 illustrates the effect of proliferation of Digoxin, Emodin and their combination on MDA 435 cell lines of Melanoma and Breast Cancer.

FIG. 7 illustrates the effect of proliferation of digoxin, Emodin and their combination on MDA 435 are cell lines of Melanoma and Breast Cancer. In this case, concentration of 1/100 had no effect (same as Control) 1/3 had good effect and 1/10 killed all cells. Normal cells were affected 50-90% less than the rate of pathological cells.

Figure 8:
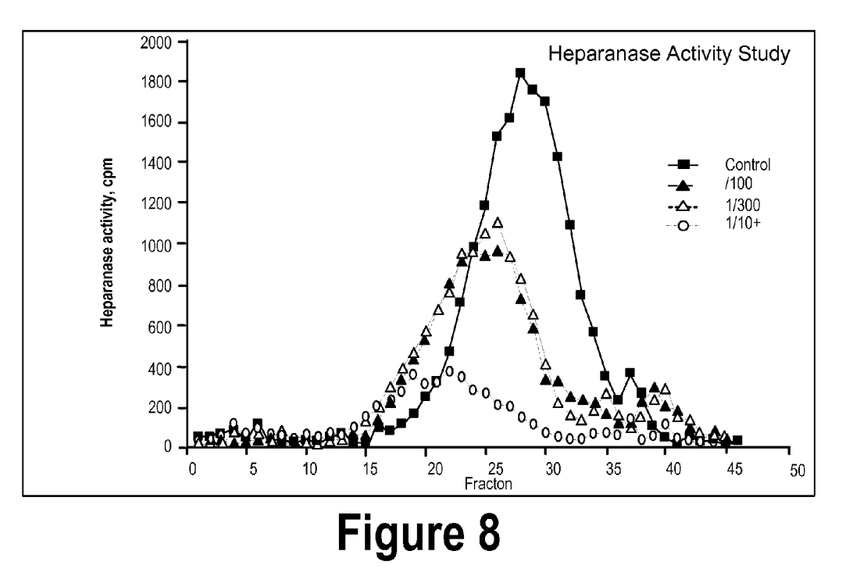
FIG. 8 illustrates the effect of proliferation of Digoxin, Emodin and their combination on Heparanase activity.

FIG. 8 illustrates the effect of proliferation of digoxin, Emodin and their combination on Heparanase activity. Heparanase is an enzyme that relates to angiogenesis (the physiological process involving the growth of new blood vessels from pre-existing vessels). This slide depicts the fact that the proliferation of the combination of digoxin and Emodin delays the activity of this enzyme.

Figure 9:
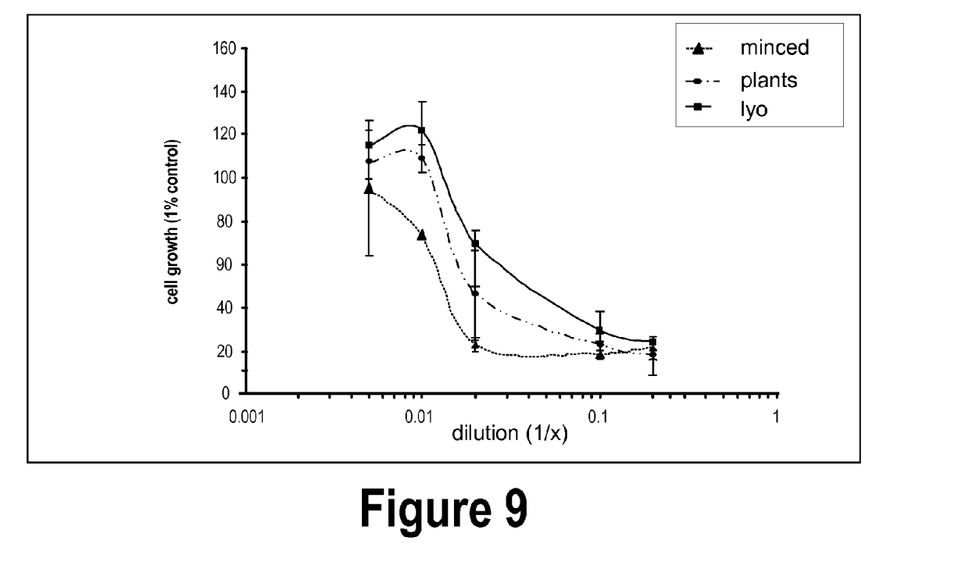
FIG. 9 illustrates the effect of proliferation of Digoxin, Emodin and their combination on HMVEC activity.

FIG. 9 illustrates the effect of proliferation of digoxin, Emodin and their combination on HMVEC which is also an enzyme that is related to angiogenesis.

Figure 10:
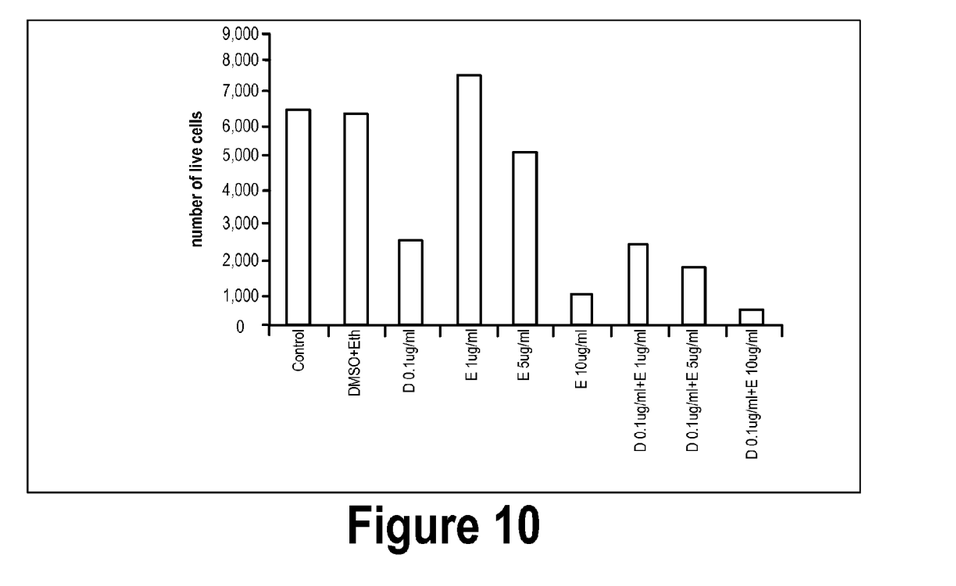
FIGS. 10-11 illustrates the effect of proliferation of Digoxin, Emodin and their combination on NB-4 Cell Line for AML (Acute Milo Leukemia).
Figure 11:
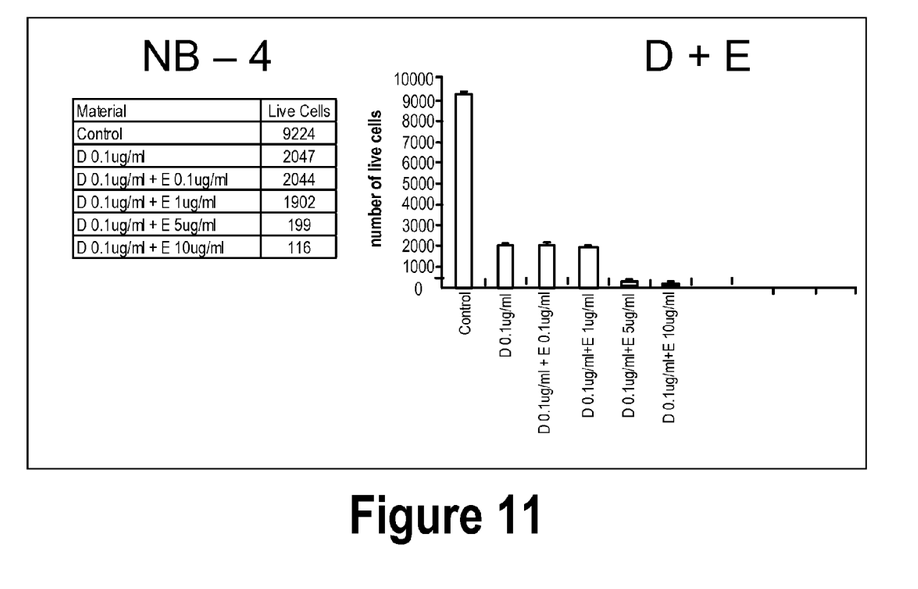

FIGS. 10 and 11 illustrate the effect of proliferation of digoxin, Emodin and their combination on NB-4 is Cell Line for AML (Acute Milo Leukemia). The two left bars in the diagram of FIG. 10 are Control (DMSO as well). The Digoxin alone 0.1 ug/ml (illustrated by the 3rd bar) shows a strong effect. Emodin alone has an effect only in large concentration (approximately 10 ug/ml or more). The three bars to the right in FIG. 10 are the effect of the combination of Digoxin and Emodin. Taking Digoxin 0.1 ug/ml and Emodin 10 ug/ml has a very strong effect better than either of the two acting alone. In fact, the effect is more than double with 892 live cells measured when Emodin alone is used, and 892 when Digoxin alone is used, and 371 were measured when both Digoxin and Emodin were used in combination. This surprising effect of the combination of Digoxin and Emodin shows an advantageous feature of the present invention.

Figure 12:
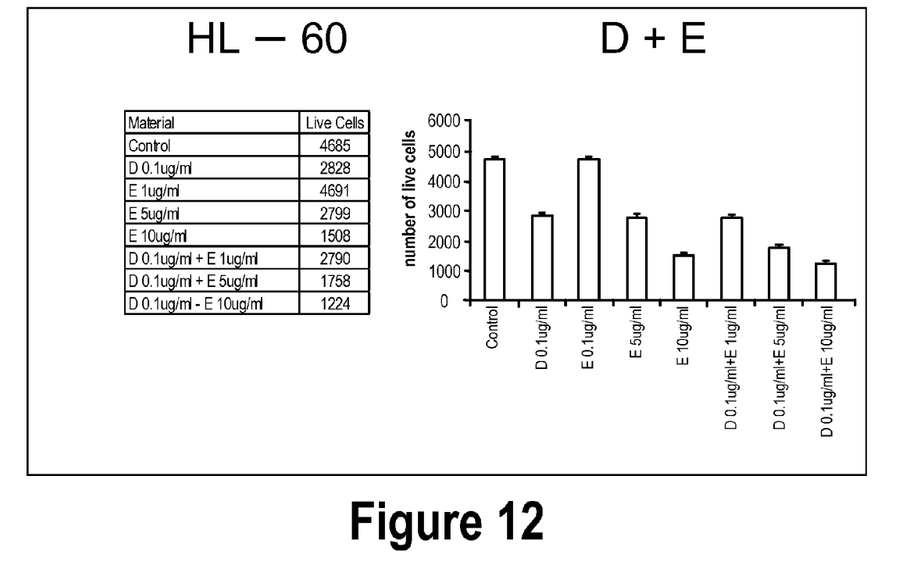
FIG. 12 illustrates the effect of proliferation of Digoxin, Emodin and their combination on HL-60 Cell Line.
Figure 13:
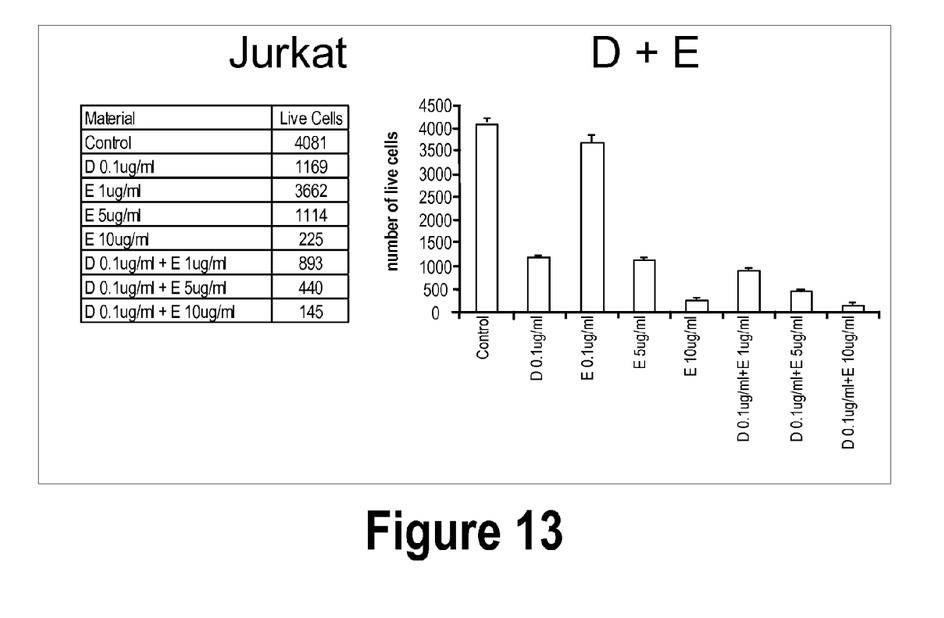
FIG. 13 illustrates the effect of proliferation of Digoxin, Emodin and their combination on Jurkat cell line.

FIGS. 12-13 show that for HL-60, which is Promyolitic Leukemia, as well as for Jurkat, which is Acute T cell Leukemia, the same surprisingly advantageous synergistic effect was observed.

Figure 14:
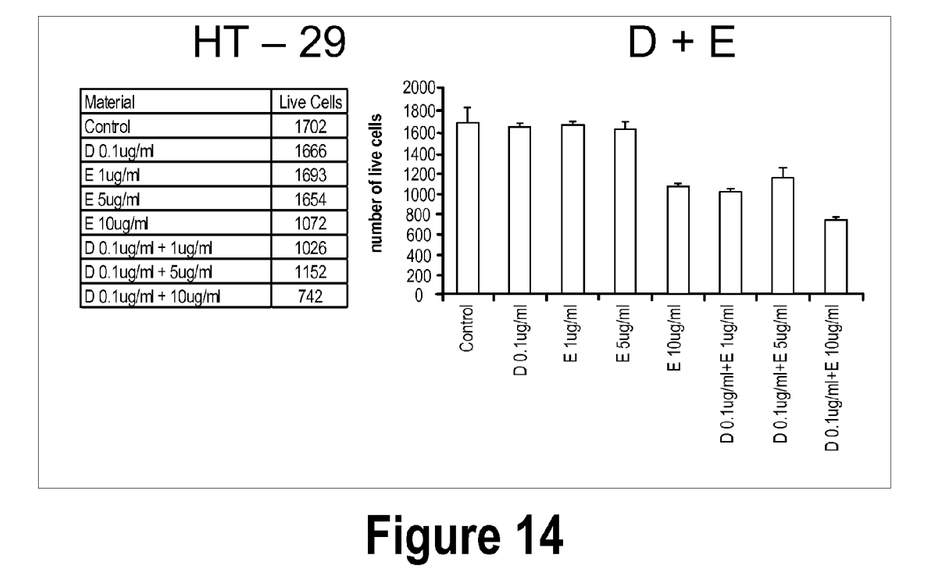
FIG. 14 illustrates the effect of proliferation of Digoxin, Emodin and their combination on HT-29 cell line.

FIG. 14 also shows a synergistic advantage of using the combination of Digoxin and Emodin on the HT-29 cell line.

EXAMPLES

The embodiments of the present invention are directed to advantageous medicines and methods of treatment and preparation of medicines and treatments for cancer wherein combinations of digoxin "D" and emodin "E" are used to inhibit tumor cell growth. The effect of CXCR4 antagonists on the survival of NB4, HL60, Jurkat leukemic cells and HT29 colon cancer and prostate tumor cells was examined. Digoxin significantly inhibited the growth of leukemic cells at concentrations between (0.05-to 1 microgram/ml). Emodin by itself inhibited the growth of leukemic cells only at concentration upper than 5 microgrm/ml. Combination of digoxin at concentration of 0.1 microgram/and either 5 or 10 microgram/ml of emodin increased significantly the tumor killing ability of both compounds. Digoxin, Emodin, and their combination also add partial however significant effect on HT29 tumor cells.

The effect of the effect of on proliferation of digoxin, Emodin, and their combination on the viability of cancer cell lines from different origin was studied. Harvested non adherent human hematopoietic cancer cell lines NB4, HL60 and Jurkat, cells were seeded at 2×105 viable cells/1 ml per well into a 24-well plate in triplicates in a medium supplemented with 10% FCS and incubated with different concentrations of digoxin, Emodin, and their combination for 24 hours. Following the incubation, the cells were stained with propidium iodide (PI) (Sigma, St. Louis, Mo.) and percent of viable PI-negative cells in culture was determined by FACScalibur analysis (Becton Dickinson Immunocytometry Systems), using CellQuest software. Adherent prostate cancer PC3 cells and colon cancer HT29 cells were seeded at 1×105 viable cells/1 ml per well into a 24-well plate under conditions described above, and following 24-hours exposure to digoxin, Emodin, and their combination, the cells were harvested, washed with PBS and stained with PI and counted as described for hematopoietic cells.

The therapeutic index of digoxin is understood to be between 0.125 m"g to 0.5 m"g, while the LD50 values of emodin in mice are understood to be 0.56 g/k"g.

When combining D and E in accordance with the present invention, there is a surprising and unexpected symbiotic effect.

The current treatment may be prepared as a mixture of herbs that are known to have separately digoxin "D" and emodin "E". Aloe-emodin is a natural anthraquinone compound that is present in some traditional medicinal plants such as Rhei Rhizoma and Rheum palmatum. Interestingly, aloe-emodin has been found to have lesser cytotoxicity towards the normal human cells. In-vitro tests with D&E molecules synthesized have been performed on a cell-line. The in-vitro with the plants was similar to the one with the isolated molecules.

Emodin may be extracted from "traditional medicinal plants such as Rhei Rhizoma and Rheum Palmatum." In one embodiment, the source of Emodin used is Da Huang—Chinese name, or Rhubarb Root—English name, or Rheum Plamatum—Botanical name, or Radix Rhisoma Rhei—Pharmaceutical name. Emodin may be extracted from Rhubarb, Buckthorn and/or Japanese Knotweed (Fallopia Japonica). Aloe-emodin may be used which is a variety of emodin found in Socotrine, Barbados, and Zanzibar aloes.

A medicinal cancer treatment using Emodin is prepared in certain embodiments by mixing the herb in water at a ratio of approximately 10:1. The herb may be ground to a fine powder. The water may be added to the fine powdered herb, and the pot covered. After boiling, the heat is lowered in certain embodiments to about 70 degrees centigrade. The acqueous mixture is cooked for another hour. The liquid is then strained into a container. In some cases, this may be done twice. In the second cooking, the ratio may be reduced to 7.5:1. The second cooking may take about 45 minutes including the boiling.

The source of Digoxin in certain embodiments is Sheng Di Huang-Chinese name, or Foxglove root—English name, or Radix Rhemania—Pharmaceutical name. The preparation of the Digoxin may the same as for the Emodin. In certain embodiments, the herbs from which the Emodin and Digoxin are extracted are cooked together. Digoxin may be extracted from Digitalis Purpurea or Purple Foxglove.

Both harvested non adherent human hematopoietic cancer cell lines NB4 (AML), HL60 and Jurkat, cells were seeded at 2×105 viable cells/1 ml per well into a 24-well plate in triplicates in a medium supplemented with 10% FCS and incubated with different concentrations of digoxin, Emodin, and their combination for 24 hours. Following the incubation, the cells were stained with propidium iodide (PI) (Sigma, St. Louis, Mo.) and percent of viable PI-negative cells in culture was determined by FACScalibur analysis (Becton Dickinson Immunocytometry Systems), using CellQuest software. Adherent prostate cancer PC3 cells and colon cancer HT29 cells were seeded at 1×105 viable cells/1 ml per well into a 24-well plate under conditions described above, and following 24-hours exposure to digoxin, Emodin, and their combination, the cells were harvested, washed with PBS and stained with PI and counted as described for hematopoietic cells.

The cancer treatment including administering a cocktail including a combination of emodin and digoxin may be combined with other treatments such as may be understood by those skilled in the art and/or as may be described in literature which are hereby incorporated by reference as disclosing alternative embodiments and compounds that may be combined with an emodin, digoxin cocktail in an effective cancer therapy.

It is also believed that treatment with an advantageous combination of Emodin and Digoxin may be provided to treat other ailments such as psoriasis and inflammatory disease.

While the invention has been described in terms of several embodiments, those skilled in the art will recognize that the invention is not limited to the embodiments described, but can be practiced with modification and alteration within the spirit and scope of the appended claims. The description is thus to be regarded as illustrative instead of limiting of the invention as set forth in the appended claims including structural and functional equivalents thereof.

While an exemplary drawing and specific embodiments of the present invention have been described and illustrated, it is to be understood that that the scope of the present invention is not to be limited to the particular embodiments discussed. Thus, the embodiments shall be regarded as illustrative rather than restrictive, and it should be understood that variations may be made in those embodiments by workers skilled in the arts without departing from the scope of the present invention, as set forth in the claims below and structural and functional equivalents thereof.

In addition, in methods that may be performed according to preferred embodiments herein and that may have been described above, the operations have been described in selected typographical sequences. However, the sequences have been selected and so ordered for typographical convenience and are not intended to imply any particular order for performing the operations, unless expressly set forth or understood by those skilled in the art being necessary.

What is claimed is:

1. A method of treating leukemia, melanoma, or colon, prostate or breast cancer comprising administering to a patient diagnosed with leukemia, melanoma, or colon, prostate or breast cancer a treatment regimen comprising the step of administering periodic doses of an effective amount of digoxin in combination with approximately 5 ug/ml or more of emodin.

2. The method of 1, wherein the periodic doses comprise more than approximately 10 ug/ml of emodin.

3. The method of 1, wherein the periodic doses comprise approximately 10 ug/ml emodin.

4. The method of 1, wherein the periodic doses comprise more than approximately 0.05 ug/ml of digoxin.

5. The method of 1, wherein the periodic doses comprise approximately 0.1 ug/ml digoxin.

6. The method of 1, wherein the periodic doses comprise approximately 10 ug/ml of emodin and approximately 0.05 ug/ml or more of digoxin.

7. The method of 1, wherein the periodic doses comprise approximately 10 ug/ml emodin and approximately 0.10 ug/ml digoxin.

8. The method of 1, wherein the periodic doses comprise approximately 10 ug/ml or more of emodin and approximately 0.05 ug/ml or more of digoxin.

9. The method of 1, wherein the periodic doses comprise between approximately 5 and 10 ug/ml of emodin and between approximately 0.05 and 0.1 ug/ml of digoxin.

10. The method of 1, wherein the treatment regimen comprises twice daily doses.

11. The method of 1, wherein the treatment regimen comprises daily doses.

12. The method of 1, wherein the treatment regimen comprises multiple doses per week.

13. The method of 1, comprising varying doses of each of the emodin and digoxin.

14. A method of treating leukemia, melanoma, or colon, prostate or breast cancer comprising administering to a patient diagnosed with leukemia, melanoma, or colon, prostate or breast cancer a treatment regimen comprising the step of administering periodic doses of an effective amount of digoxin in combination with approximately 5 ug/ml or more of emodin or the step of administering an effective amount of digoxin in combination with approximately 5 ug/ml or more of emodin with DMSO.

15. The method of claim 14, comprising varying doses of each of the emodin and digoxin.

16. The method of claim 14, wherein the periodic doses 10 ug/ml or more of emodin.

17. The method of claim 14, wherein the periodic doses comprise approximately 10 ug/ml of emodin.

18. The method of claim 14, wherein the periodic doses comprise approximately 0.05 ug/ml or more of digoxin.

19. The method of claim 14, wherein the periodic doses comprise approximately 0.10 ug/ml digoxin.

20. The method of claim 14, wherein the periodic doses comprise approximately 10 ug/ml of emodin and approximately 0.05 ug/ml or more of digoxin.

21. The method of claim 14, wherein the periodic doses comprise approximately 10 ug/ml or more of emodin and approximately 0.10 ug/ml of digoxin.

22. The method of claim 14, wherein the periodic doses comprise approximately 10 ug/ml or more of emodin and approximately 0.05 ug/ml or more of digoxin.

23. The method of claim 14, wherein the periodic doses comprise between approximately 5 and 10 ug/ml of emodin and between approximately 0.05 and 0.1 ug/ml of digoxin.

24. The method of claim 14, wherein the treatment regimen comprises twice daily doses.

25. The method of 1, wherein the treatment regimen comprises daily doses.

26. The method of 1, wherein the treatment regimen comprises multiple doses per week.

27. The method of 1, wherein the emodin has been extracted from rhubarb root.

28. The method of claim 14, wherein the emodin has been extracted from rhubarb root.

29. The method of 1, wherein the emodin has been extracted from rhubarb, Buckthorn, and/or Japanese Knotweed.

30. The method of claim 14, wherein the emodin has been extracted from rhubarb, Buckthorn, and/or Japanese Knotweed.

31. The method of 1, wherein the periodic doses comprise 1.0 ug/ml of digoxin.

32. The method of claim 31, wherein the periodic doses comprise 0.05 ug/ml or more of digoxin.

33. The method of claim 31, wherein the periodic doses comprise 0.1 ug/ml or more of digoxin.

34. The method of claim 14, wherein the periodic doses comprise approximately 1.0 ug/ml of digoxin.

35. The method of claim 34, wherein the periodic doses comprise 0.05 ug/ml or more of digoxin.

36. The method of claim 34, wherein the periodic doses comprise 0.1 ug/ml or more of digoxin.

37. The method of 1, wherein the patient has been diagnosed with melanoma.

38. The method of claim 14, wherein the patient has been diagnosed with melanoma.

39. The method of 1, wherein the patient has been diagnosed with breast cancer.

40. The method of claim 14, wherein the patient has been diagnosed with breast cancer.

* * * * *